United States Patent

Huskey et al.

[11] Patent Number: 5,690,628
[45] Date of Patent: Nov. 25, 1997

[54] REFASTENABLE ADHESIVE TAPING SYSTEM

[75] Inventors: Richard A. Huskey, Mentor, Ohio; Eng-Pi Chang, Arcadia, Calif.; Carol A. Caldwell, Kirtland Hills; Gary A. Avalon, Painesville, both of Ohio; Yung-Hsiang Huang, Appleton, Wis.; Dave A. Soerens, Neenah, Wis.; Ruth A. Lachapell, Menasha, Wis.

[73] Assignee: Avery Dennison Corporation, Pasadena, Calif.

[21] Appl. No.: 376,284

[22] Filed: Jan. 20, 1995

Related U.S. Application Data

[63] Continuation of Ser. No. 57,004, May 3, 1993, abandoned.

[51] Int. Cl.$^6$ .................... A61F 13/15; B32B 7/12
[52] U.S. Cl. ................... 604/390; 604/389; 428/355
[58] Field of Search ..................... 604/358, 365–366, 604/385.1, 389–391; 428/355

[56] References Cited

U.S. PATENT DOCUMENTS

| | | |
|---|---|---|
| 4,460,364 | 7/1984 | Chen et al. . |
| 4,762,888 | 8/1988 | Sun et al. . |
| 4,861,635 | 8/1989 | Carpenter et al. . |
| 4,879,178 | 11/1989 | Sun et al. . |
| 4,988,742 | 1/1991 | Moon et al. . |
| 5,024,880 | 6/1991 | Veasley et al. . |
| 5,147,347 | 9/1992 | Huang . |
| 5,217,798 | 6/1993 | Brady et al. . |
| 5,232,702 | 8/1993 | Pfister et al. . |
| 5,458,983 | 10/1995 | Wang et al. . |
| 5,462,546 | 10/1995 | Caldwell . |

FOREIGN PATENT DOCUMENTS 0306232  8/1988  European Pat. Off. .

OTHER PUBLICATIONS

Ferry, J.D., Viscoelastic Properties of Polymers, 3rd Ed., 1980, pp. 46–47, John Wiley & Sons.

*Primary Examiner*—Mary Beth Jones
*Assistant Examiner*—K. M. Reichle
*Attorney, Agent, or Firm*—Pearne, Gordon, McCoy & Granger

[57] ABSTRACT

A refastenable diaper is provided with a securing zone on the diaper outer cover of a peak strength of less than 2750 grams/inch. A refastenable adhesive taping system for the diaper includes an adhesive fastening tape comprising a flexible backing and a layer of pressure-sensitive adhesive permanently combined to said flexible backing and adapted to be applied to and released from the securing zone to fasten and open the diaper. The adhesive exhibits a 180° peel adhesion of the tape to the securing zone that is less than the peak strength of the securing zone. The adhesive is selected to be within a specified rheological window, that is, have a maximum tan delta, or (tan delta)$_{max}$, of from 1.5 to 2.5 at 20° C., reached at a frequency, or $(w)_{max}$, of greater than 500 rad/sec.

51 Claims, 1 Drawing Sheet

REFASTENABLE ADHESIVE TAPING SYSTEM

This is a continuation of application Ser. No. 08/057,004, filed May 3, 1993, now abandoned.

This invention relates to refastenable taping systems for diapers. The invention is particularly applicable in refastenable taping systems for diapers whose securing zones that releasably receive the adhesive fastening tape have relatively low peak strengths.

BACKGROUND

For a disposable diaper to be acceptable in the consumer market, its adhesive fastening tapes must be capable of being peeled away easily without significantly stretching the diaper outer cover during the unfastening-refastening process. At the same time, the fastened tape must sustain forces applied intermittently due to vigorous motion by the infant or other wearer without popping open when the diaper is in use.

To meet these two conditions, most diapers on the market use an aggressive pressure-sensitive-adhesive for their fastening tape (an adhesive which establishes a peel strength at the tape-to-diaper interface considerably exceeding the peak strength of the diaper outer cover), together with a strong reinforcing tape or patch on or under the diaper outer cover at its tape-receiving securing zone.

The peel behavior of a diaper tape closure system depends on how fast the tape is removed from the substrate. At low speeds, the peel is smooth and peel adhesion increases with increasing speed. However, when the speed exceeds a certain rate, peel adhesion will drop and, in most cases, the peel will become "shocky." Shocky behavior is often referred to in the literature as "stick-slip" peel, and is also referred to as "zippy" peel. Shocky peel is typically quite noisy.

The speed at which the transition from smooth peel to shocky peel occurs can be called the transition speed of a tape closure system. Peel adhesion reaches the maximum at the transition speed. It should be noted that the phenomenon of transition does not always occur. If peel adhesion exceeds the peak or yield strength of the substrate before the transition speed is reached, the substrate will be stretched, and transition from smooth peel to shocky peel will not happen.

Since there is a significant change in peel characteristics at the transition speed, the level of the transition speed will affect the performance as well as the user's perception of a diaper tape closure system. If the transition speed is low, upon peeling, the person opening the tape immediately experiences a high resistance to peel which is then followed by a drop in peel resistance. On the other hand, if the transition speed is high, the person opening the tape will experience a gradual increase in peel resistance until the transition speed is reached. The latter case gives the consumer a feeling of "easy peel."

As stated above, most diapers on the market use a strong reinforcing tape or patch at the securing zone. Some adult diapers do not use reinforcing tapes or patches, but the transition speeds for those taping systems are quite low, below 2000 mm/min, implying adhesive fastening performance which is unsatisfactory for infant use and in other applications where the noises which occur above transition speed are objectionable, and where it is desirable to eliminate or minimize noises associated with shocky peel. Diapers with taping systems of such low transition speeds are therefore outside the range of present interest.

BRIEF DESCRIPTION OF THE INVENTION

The present invention involves the concept of applying certain rheological criteria in order to combine, in a novel manner, relatively high transition speeds and relatively low (but not too low) maximum peel adhesions, thereby achieving a desirable balance of adhesive fastening performance characteristics in a diaper, including minimizing or eliminating the noise associated with shocky peel, and also accomplishing, if desired, elimination of special reinforcing patches at the securing zone of the diaper.

As a loud noise will typically be generated when peel speed or removal speed exceeds the transition speed, increasing the transition speed helps avoid or minimize startling or disturbing effects on infant wearers when diapers are changed or inspected, particularly at quiet times when infants are asleep or drowsy. A higher transition speed will maintain the smooth peel mode longer, thus reducing the amount of noise generated. If the transition speed is greater than maximum actual removal speed, the former will not be reached during peel, and generation of noise associated with shocky peel will be avoided altogether.

However, since peel adhesion increases with peel speed until the transition speed is reached, increasing the transition speed also tends to increase the maximum peel adhesion of the system. This can cause a problem of substrate deformation or tearing for diapers with low securing zone strength. There has long been a need in the industry to provide a way to ameliorate or eliminate this problem, if possible, thus allowing higher transition speeds without experiencing unduly high maximum peel adhesion. The present invention discloses adhesive selection within specified rheological windows so as to accomplish this object. The invention controls both the transition speed and the maximum peel adhesion at the same time, tailoring them by means of the selection of rheological properties.

The theological properties referred to are (a) (tan delta)$_{max}$ or maximum tan delta (max tan $\delta$) and (b) (w)$_{max}$ or frequency at which the maximum tan delta occurs. The tan delta (dynamic mechanical loss tangent) of a pressure sensitive adhesive is a rheological property defined as the ratio of G" (dynamic loss shear modulus) to G' (dynamic storage shear modulus). Both G' and G" can be measured under a dynamic experiment where the adhesive is subjected to oscillatory shear motion. For a given adhesive, measurement of tan delta over a range of frequencies will result in a maximum measured tan delta value at one frequency in the range. See Ferry, John D., *Viscoelastic Properties of Polymers*, John Wiley & Sons, 1980. It has been previously recognized in a general way that transition speed depends primarily on the viscoelastic behavior of the adhesive, see U.S. Pat. No. 5,147,347, of partial common inventorship with the present invention, at col. 10, line 47. However, the transition speeds there contemplated are very low due to perceived inability to combine relatively high transition speeds and relatively low maximum peel adhesions. The present invention recognizes that the maximum tan delta and the frequency at which the maximum tan delta occurs are unique to the viscoelastic properties of an adhesive in such a way that there is a rheological window allowing the desired tailoring of both transition speed and the maximum peel adhesion.

Unreinforced securing zones of diapers typically have peak strengths less than 2750 grams/inch, and preferably the diaper materials are such that the securing zone peak strength is less than 1500 grams/inch, since the use of light, thin web materials is desirable from the standpoint of wearer comfort, material cost, and performance factors such as flexibility, softness, and conformability. The invention provides control of the transition speed and maximum peel adhesion for a diaper having such securing zone peak strengths.

The transition speed for such systems should be greater than 2000 mm/min and preferably greater than 3000 mm/min. In other words, the fastening system should exhibit a smooth peel at a speed greater than 2000 mm/min, and preferably at a speed greater than 3000 mm/min. For the system to exhibit such high transition speeds, the frequency at which the tan delta reaches the maximum should be greater than 500 rad/sec, and preferably greater than 3000 rad/sec at 20° C.

To avoid securing zone stretching or tearing, the maximum peel adhesion of the system is chosen to be less than the peak strength of the securing zone, and preferably less than about 55–60% of peak strength, or less than 2750 grams/inch and preferably less than 1500 grams/inch for diapers whose securing zone peak strength is less than 2750 grams/inch, or less than 1500 grams/inch and preferably less than 900 grams/inch for diapers whose securing zone peak strength is less than 1500 grams/inch. In the described context, a maximum tan delta of the adhesive of not more than 2.5 or more preferably 2.0 at 20° C. will generally provide such maximum peel adhesions, while a maximum tan delta of at least 1.5, and preferably at least 1.7, will provide peel adhesions such that the tape fastenings are sufficiently secure. In sum, the adhesive should be selected such that it exhibits a maximum tan delta between 1.5 and 2.5, and preferably between 1.7 and 2.0, at 20° C., and such that the frequency at which the tan delta reaches the maximum is as specified above.

The result is a diaper tape fastening system having a desirable balance of adhesive fastening performance characteristics, in which the noise associated with shocky peel may be minimized or eliminated, and in which special reinforcing patches at the securing zone of the diaper may be eliminated if desired.

DETAILED DESCRIPTION OF THE INVENTION

This detailed description of the invention is made in the context of a refastenable disposable diaper for infants and young children. However, the invention can be used for refastenable diapers for incontinent adults, for other disposable absorbent garment articles, or for other articles using refastenable adhesive closures such as gowns, aprons, feminine care articles, and the like. Reference in the claims to a refastenable diaper will be understood to refer to all such articles.

The context of the invention set forth in this detailed description is similar to the context of the invention of U.S. Pat. No. 5,147,347 which also deals with diapers of low securing zone strength; however such prior patent discloses an invention pertaining to selecting fastening tape backing rigidity such as to come within a specified ratio range, with reference to the ratio between fastening tape rigidity and securing zone rigidity, whereas the present invention pertains to selecting fastening tape adhesive to come within specified rheological windows. Such prior patent does not disclose the windows for rheological properties which accomplish both desirable transition speed and desirable peel adhesion, as presently disclosed, However, due to the similarity in context, much of following the contextual description repeats that of said patent.

Figure 1:
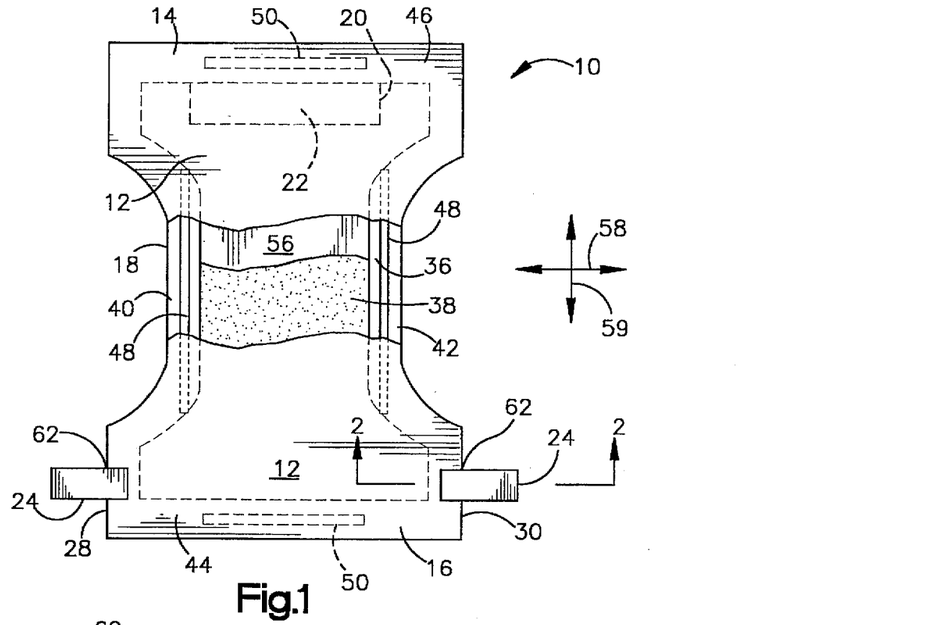
FIG. 1 is a somewhat diagrammatic plan view, partly in section, of a disposable diaper in which the invention is employed.

With reference to FIG. 1, a representative article of the invention, such as diaper 10, comprises a flexible outer layer, such as outer cover layer or outer shell 12. The outer cover has waistband sections 14 and 16 positioned at opposite ends of the outer cover, and has an intermediate section 18 which interconnects the waistband sections. The outer cover includes a securing zone substrate 20 which is located over at least a portion of a first of the waistband sections, such as front waistband 14. The securing zone is generally defined by the area within the dotted lines, and provides a landing surface 22 appointed for receiving adhesion of one or more adhesive tabs 24 thereon. Securing zone 20 has a selected peak strength and may have a selected rigidity value. An adhesive tab 24 is suitably located and attached at at least one lateral side edge 28, 30 of a second of said waistband sections, such as rear waistband section 16, for securing the waistband sections around a wearer. Each adhesive tab 24 includes a backing layer 32 and an adhesive layer 34. When adhered to landing surface 22, the adhesive tab has a 180° peel adhesion value which is less than the peak strength of securing zone 20. The adhesive 34 is selected such that its maximum tan delta is between 1.5 and 2.5, and preferably between 1.7 and 2.0, at 20° C., and the frequency at which the tan delta reaches the maximum is greater than 500 rad/sec, and preferably greater than 3000 rad/sec at 20° C.

The illustrated diaper 10 has a front waistband region 12, a back waistband region 16, an intermediate crotch region 18, and a periphery which is defined by the outer margins of the diaper in which the longitudinal margins are designated 40 and 42, and the end margins are designated 44 and 46. The diaper additionally has a transverse width direction 58 and a longitudinal length direction 59.

The shown configuration of diaper 10 is generally "hourglass" shaped or I-shaped with a central, narrowed intermediate crotch section 18 and relatively wider waistband sections 14 and 16. Optionally, the garment may have some other shape which is suitable for its intended use. For example, the diaper may have a generally rectangular shape, or a T-shape with the relatively wider, cross-arm of the "T" forming either the front or rear waistband section of the diaper.

The illustrated embodiment includes at least one adhesive tab located at each lateral side edge of rear waistband section 16. In addition, diaper 10 includes a topsheet layer or inner shell 36 superposed in facing relation with outer cover 12, and an absorbent body 38 located between outer cover 12 and the topsheet. Either or both of outer cover 12 and topsheet 36 may extend past the lateral side edges of absorbent body 38 to form diaper side margins 40 and 42. In addition, either or both of outer cover 12 and topsheet 36 may extend past the longitudinal end edges of absorbent body 38 to form diaper end margins 44 and 46. In the illustrated embodiment, outer cover 12 and topsheet 36 are essentially coterminous and extend past both the lateral and longitudinal edges of the absorbent body.

Each of the diaper side margins can include one or more individual leg elastic members 48 for providing resiliently gathered gasketing cuffs about the legs of the wearer. In addition, either or both of diaper end margins 44, 46 can include one or more individual waist elastic members 50 for providing elasticized waistbands about the waist of the wearer. The diaper may further include elasticized containment flaps, such as those described in U.S. Pat. No. 4,704,116.

The elastic members are secured to the diaper 10 in an elastically contractible condition so that under normal conditions the elastic members will operably contract the associated margins of diaper 10. The elastic members can be secured in an elastically contractible condition in at least two ways, for example, the elastic members 34 may be stretched and then secured to diaper 10 while the diaper is in an uncontracted condition. Alternatively, the diaper 10 may be contracted, for example by pleating, and the elastic members then secured and connected to the diaper 10 while the elastic member are in their relaxed or unstretched condition. Still other techniques, such as the incorporation of heat-shrink elastic material, may be used to gather the garment.

In the embodiment illustrated in FIG. 1, leg elastic members 48 extend essentially the length of intermediate crotch region 18 of diaper 10. Alternatively, the leg elastics may extend the entire length of the diaper 10, or any other length suitable for providing the arrangement of elastically contractible lines desired for the particular diaper design.

The elastic members may have any of a multitude of configurations. For example, the width of the individual elastic members may be varied from 0.25 millimeters (0.01 inches) to 25 millimeters (1.0 inches) or more. The elastic members 48 may comprise a single strand of elastic material or may comprise several separated, parallel or non-parallel strands of elastic material, and the elastic members may be applied in a rectilinear or curvilinear arrangement. In addition, the elastic members may be composed of natural rubber or a synthetic rubber, such a polyurethane elastomer, DuPont "LYCRA" elastomer or the like.

The various components of diaper 10 can be assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying adhesive droplets or filaments, or by employing a plurality of generally parallel lines of hot melt pressure-sensitive adhesive oriented along the length direction of the diaper. In the shown embodiment of the invention, the diaper component elements are assembled together by employing a patterned adhesive comprising a plurality of juxtaposed, looping arrays of swirled adhesive filaments which are laid down generally along the length dimension of the diaper.

Outer cover 12 may be composed of a liquid-permeable material, but typically is composed of a liquid-impermeable material, such as a polyolefin sheet composed of polyethylene, polypropylene or the like. Alternatively, outer cover 12 may comprise a nonwoven fibrous web which has been suitably treated or otherwise configured to impart a desired level of liquid impermeability. In particular embodiments of the invention, outer cover 12 may comprise a liquid-impermeable, but vapor-permeable material, such as a microporous polyolefin sheet or a microporous nonwoven fibrous web.

The shown embodiment of outer cover 12 may be a polyethylene film meeting the selected strength, thickness and roughness criteria given below, for example the test substrate set forth below.

Topsheet 36 is typically composed of a liquid-permeable, substantially hydrophobic material, such as a spunbonded web composed of a synthetic polymer filaments. Alternatively, topsheet 36 may comprise a meltblown web or a bonded-carded-web composed of synthetic polymer filaments. Suitable synthetic polymers include, for example, polyethylene, polypropylene, and polyesters. The topsheet has an effective pore size that readily allows the passage therethrough of liquids, such as urine and other body exudates. Optionally, the topsheet can be treated with a surfactant to impart a desired degree of wettability, or can be selectively embossed, or can be perforated with discrete slits or holes extending therethrough.

Absorbent body 38 can comprise a liquid-retaining pad composed of airlaid hydrophilic fibers, such as cellulosic fibers commonly referred to as wood pulp fluff. Conventional pads can have a density ranging from about 0.05–0.2 gm/cc, and are sufficiently flexible to readily conform to the body of the wearer. Absorbent body 38 may also comprise a coform material composed of a mixture of cellulosic fibers and synthetic polymer fibers. For example, the coform material may comprise an airlaid blend of cellulosic wood pulp fibers and meltblown polyolefin fibers, such as fibers composed of polyethylene and/or polypropylene.

The shape of the absorbent body may be I-shaped, as representatively shown in FIG. 1, or may be generally rectangular. Alternatively, the pad shape may be T-shaped or generally oval.

Absorbent body 38 may also include an effective amount of an inorganic or organic high-absorbency material to enhance the absorptive capacity of the absorbent body. For example, absorbent body 16 can include about 5 . 95 weight percent high-absorbency material, and ordinarily includes about 10–60 weight percent of the high-absorbency material to provide desired levels of performance. Suitable inorganic high-absorbency materials include, for example, absorbent clay and silica gels. Organic high-absorbency materials can include natural materials, such as pectin, guar gum and peat moss, as well as synthetic materials, such as synthetic hydrogel polymers. Such hydrogel polymers can include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers may include hydrolyzed acrylonitrile grafted starch acrylic acid grafted starch, and isobutylene maleic anhydride copolymers, and mixtures thereof. The hydrogel polymers are preferably lightly cross-linked to render the materials substantially water insoluble. Cross-linking may, for example, be by irradiation or by covalent, ionic, Van der Waals, or hydrogen bonding. Suitable materials are available from various commercial vendors, such as Dow Chemical Company, Hoechst-Cellanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 38 employing various techniques. For example, the high-absorbency material can be substantially uniformly distributed in the fibers comprising the absorbent body. The material can also be non-uniformly distributed within the fibers to form a generally continuous gradient with either an increasing or decreasing concentration of high-absorbency material through the thickness of the absorbent body. The increasing or decreasing nature of the concentration gradient is determined by observing the concentration moving from the body side of absorbent body 38 to the outer side of the absorbent body. In an alternative arrangement, the high-absorbency material can comprise a discrete layer separate from the fibrous material of absorbent body 38, or comprise a discrete layer integral with the fibrous material of the absorbent body.

Absorbent body 38 can further include a wrap sheet 56 to help maintain the integrity of the airlaid fibrous structure and any superabsorbent particles contained therein. At least the portion of wrap sheet 56 which is positioned on the body side surface of absorbent body 38 is liquid permeable. The wrap sheet typically comprises a cellulosic material, such as a creped wadding or a high wet-strength tissue, and is commonly referred to as a tissue wrap. Optionally, the wrap sheet may comprise a woven or nonwoven web of synthetic polymer fibers.

Figure 2:
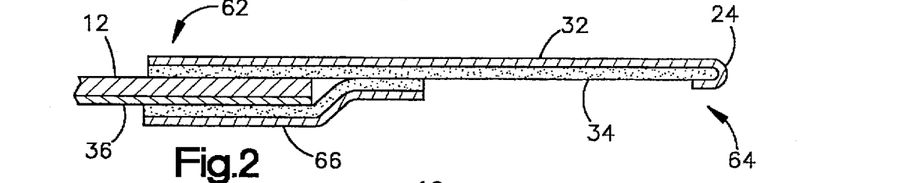
FIG. 2 is a view on the plane of line 2—2 in FIG. 1.

In diaper 10, the adhesive-type fastening system includes adhesive tape tabs 24. With reference to FIG. 2, the tape tab comprises a backing layer 32, and an adhesive layer 34 which is applied and bonded to a major surface of the backing layer. A factory bond section 62 of tab 24 is suitably attached to outer cover 12, such as by employing an adhesive bond. Alternatively, the attachment may be accomplished with thermal bonds, sonic bonds, mechanical fasteners or the like. When the tab is in a folded-over, storage position on the diaper, release layer 66 typically covers the adhesive on a user bond section 64 of the tape tab. At the appropriate time, the user separates the tab from the release layer to expose the adhesive for use in holding the diaper on an infant.

Figure 3:
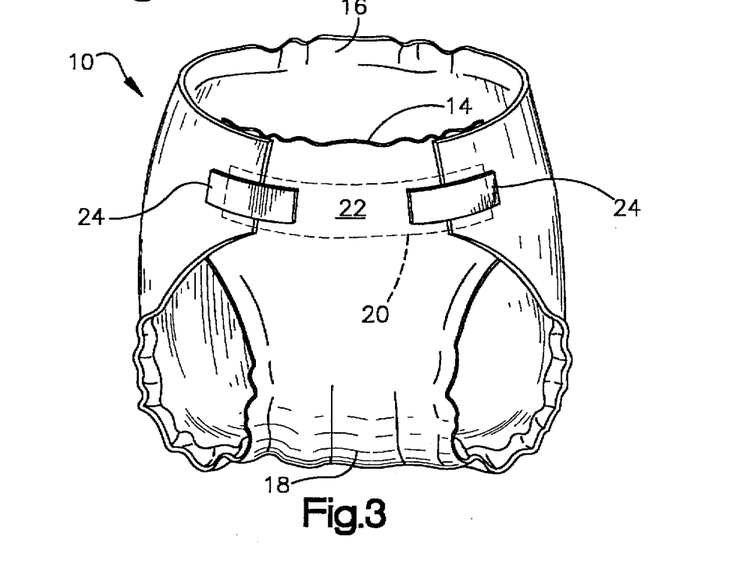
FIG. 3 is a sketch of the same diaper as worn by an infant.

When diaper 10 is worn, the waistband sections 14 and 16 of the diaper encircle the infant's waist, and intermediate section 18 extends between the infants's legs and over the infant's crotch area, as representatively shown in FIG. 3. Tape tab 24 are then employed to interconnect the lateral side edges of back waistband portion 16 to adjacently located side sections of front waistband portion 14 and thereby secure the garment on the infant.

When the diaper is first fitted onto the infant, it has been desirable to have the capability of repositioning tabs 24 on the front waistband section of diaper 10 to provide a more secure or more comfortable fit. More particularly, it has been desirable to be able to peel tape tabs 24 from adhesive contact with outer cover 12, reposition the tape tab and adhesively refasten the tab to another select portion of outer cover 12. Thereafter during use, it has been desirable to be able to check the diaper for wetness and for any other soiled condition. The user is better able to examine the diaper condition if the tape tabs can be releasably peeled from their adhesive bond with outer cover 12 to allow a further opening of the diaper for inspection. If the diaper is not soiled, it is potentially reusable, provided the diaper can be re-secured about the infant. The process of peeling tape tab 24 from outer cover 12, however, can tear the backsheet material and destroys its liquid barrier function. In addition, pieces of backsheet material can remain adhered to the tape tab and render it unserviceable. The contamination produced by the residual backsheet material on the tape tab degrades the ability of the tab to refasten onto outer cover 12.

Conventional techniques for addressing these problems have included the use of a separate, extra patch of localized reinforcing material applied to either the inner surface or outer surface of outer cover 12 to strengthen the outer cover and increase its resistance to tearing in at least the reinforced patch region of the outer cover. The patch material may, for example, be a plastic strip, a scrim material, an extra layer of adhesive or the like. The patch region provides a reinforced, strengthened area which is appointed for adhesive contact with the fastening tapes and is better able to resist stretching and tearing when the adhesive tab is peeled away from the patch region. Typically, the peel adhesion value between the adhesive tab and the appointed securing zone surface is relatively high to ensure that the movements of the wearer do not cause the adhesive tabs to loosen or pop open during use. While the reinforcing patch may incorporate selected graphics or ornamental designs, the sole structural purpose of the patch has ordinarily been to provide a reinforced and/or coordinated landing surface against which the adhesive tabs may be adhered.

The addition of supplementary reinforcing mechanisms, such as the plastic strips, scrim materials or supplemental adhesive layers described above, however, can undesirably add cost. As a result there has been a continued need for a refastenable adhesive taping system which does not include supplemental layers of reinforcing material which serve only to strengthen the appointed securing zone region of outer cover 12. To provide a more cost-effective design, it has been desirable to have a refastenable adhesive taping system which decreases the number of component elements in the finally assembled article. For example, it has been desirable to have a refastenable taping system wherein the securing zone region of outer cover 12 does not include an extra patch-like component, the primary purpose of which is to provide a specially prepared landing surface or a region of relatively higher strength at a selected area of the outer cover.

As in the invention of U.S. Pat. No. 5,147,347, in particular aspects of the present invention, the refastenable taping system can provide desired levels of adhesive performance without the use of a special reinforcing patch positioned at the tape securing zone. For example, the securing zone of outer cover 12 can comprise only the outer cover material, or may comprise a composite laminate composed of the outer cover material bonded to its immediately adjacent layer of construction material, such as the wrap sheet material placed about the absorbent pad of the article. Such adjacent layer is not localized to the securing zone 20, and has a primary structural purpose other than that of reinforcing outer cover 12.

However, additionally, the present invention can also provide improved noise performance by avoiding or minimizing startling or disturbing effects on infant wearers when diapers are changed or inspected, particularly at quiet times when infants are asleep or drowsy. That is, desired levels of adhesive performance, accompanied by both avoidance of a special reinforcing patch and improved noise performance, are achievable by the present invention.

With reference again to FIG. 1, securing zone 20 comprises a substrate region which is located at front waistband section 14 of outer cover 12. The substrate includes a landing surface 22 which is appointed for receiving the adhesion of at least one adhesive tab 24 thereon. The illustrated embodiment is constructed such that the adhesive tabs, located at each side edge 28 and 30 of rear waistband 16, will both simultaneously attach to securing zone 20 during the intended use of diaper 10. The securing zone has a peak strength of less than 2750 grams/inch and preferably less than 1500 grams/inch. The strength of the securing zone is at least 500 grams/inch and preferably at least 700 grams/inch.

The maximum peel adhesion of the system for a peel speed from 2000 mm/minute to 25000 mm/minute is chosen to be less than the peak strength of the securing zone, and preferably less than 55–60% of peak strength, or less than 2750 grams/inch and preferably less than 1500 grams/inch for diapers whose securing zone peak strength is less than 2750 grams/inch, or less than 1500 grams/inch and preferably less than 900 grams/inch for diapers whose securing zone peak strength is less than 1500 grams/inch. These maximum values can accomplish avoidance of securing zone stretching or tearing. In the described context, a maximum tan delta of the adhesive of not more than 2.5 or more preferably 2.0 at 20° C. will provide such maximum peel adhesions, while a maximum tan delta of at least 1.5, and preferably at least 1.7 at 20° C., will provide peel adhesions such that the tape fastenings are sufficiently secure. In sum, the pressure-sensitive adhesive should be selected such that it exhibits a maximum tan delta between 1.5 and 2.5, and preferably between 1.7 and 2.0, at 20° C., and such that the frequency at which the tan delta reaches the maximum is as specified above.

Examples of the invention that are embodied in the following tests are set forth for purposes of illustration only, and are not intended to limit the scope of the invention.

TESTS

Tests were conducted using the adhesives identified in the Table of Test Adhesives set forth below. The tests were conducted using the three substrates identified below. The test results are set forth in the following table.

TABLE OF TEST RESULTS

Col. A   Test number.
Col. B   Adhesive (see Table of Test Adhesives).
Col. C   Substrate selected peak, strength, gm/inch.
Col. D   Transition speed, mm/min.
Col. E   $(w)_{max}$. Frequency for max tan delta, rad/sec.
Col. F   Maximum peel adhesion, gm/inch.
Col. G   (tan delta)$_{max}$. Maximum tan delta, dimensionless.

| A | B | C | D | E | F | G |
|---|---|---|---|---|---|---|
| 1 | a | 950 | 2200–2400 | 1720–3390 | 450 | 1.71 |
| 2 | e' | 950 | >3000 | 1730–2930 | >615 | 2.09 |
| 3 | b | 950 | 14000–15000 | 7000–10400 | 550 | 1.81 |
| 4 | c | 950 | 500–700 | 120 | 425 | 1.70 |
| 5 | d | 950 | — | 18–26 | tear | 3.18 |
| 6 | a | 1080 | 3000–3500 | 1720–3390 | 520 | 1.71 |
| 7 | e' | 1080 | 12000–13000 | 1730–2930 | 860 | 2.09 |
| 8 | b | 1080 | 17000–20000 | 7000–10400 | 680 | 1.81 |
| 9 | e | 1080 | 6500–7500 | 1100–1800 | 710 | 2.09 |
| 10 | f | 1080 | 7100–7260 | 2380–2690 | 670 | 2.13 |
| 11 | g | 1080 | 7250–7500 | 4200–6700 | 540 | 1.75 |
| 12 | c | 1080 | 500–700 | 120 | 390 | 1.70 |
| 13 | d | 1080 | — | 18–26 | tear | 3.18 |
| 14 | h | 1080 | 1700–1750 | 620–1730 | 660 | 2.20 |
| 15 | i | 1080 | 550–600 | 155–245 | 680 | 2.43 |
| 16 | e' | 2550 | 12000–13000 | 1730–2930 | 1090 | 2.09 |
| 17 | e | 2550 | 10000–11000 | 1100–1800 | 1140 | 2.09 |
| 18 | f | 2550 | 15000–17500 | 2380–2690 | 960 | 2.13 |
| 19 | g | 2550 | 23000–25000 | 4200–6700 | 960 | 1.75 |
| 20 | h | 2550 | 2000–2200 | 610–970 | 1060 | 2.20 |

TABLE OF TEST ADHESIVES

| ADHESIVE DESIGNATION | K1107 or 1117[1] | E1310[2] | WT10[3] |
|---|---|---|---|
| | (WEIGHT %)[4] | | |
| a | 49.15 | 39.32 | 9.83 |
| b | 49.15 | 29.49 | 19.66 |
| c | 49.50 | 49.50 | 1.00 |
| d | 29.49 | 49.15 | 19.66 |
| e | 42.30 | 36.39 | 19.66 |
| e' | 42.22 | 36.33 | 19.06 |
| f | 42.63 | 32.78 | 22.93 |
| g | 49.15 | 29.49 | 19.66 |
| h | 39.32 | 39.32 | 19.66 |
| i | 36.60 | 44.51 | 17.18 |

Footnotes:
[1] K1107 and K1117: "KRATON" 1107 and "KRATON" 1117, polystyrene-isoprene-polystyrene linear block, copolymers, Shell Chemical Co. Adhesive c is formulated with "KRATON" 1117, all others with "KRATON" 1107.
[2] E1310: "ESCOREZ" 1310LC, a solid $C_5$ tackifying resin, Exxon Chemical Corp.
[3] WT10: "WINGTACK" 10, a solid $C_5$ tackifying resin, Goodyear Chemical Co.
[4] Each adhesive composition also includes from 0.2 to 1.5% "ETHANOX" 330 and "PLASTONOX LDTP" antioxidants. "ETHANOX" 330 is a phenolic antioxidant sold by Ethyl Corporation. "PLASTONOX LDTP" is a thioester antioxidant sold by American Cyanamid Company.

Test substrate I has a peak tensile strength of about 950 grams/inch. It is composed of a thin polyethylene film having a thickness of 1.25 mils laminated with a layer of tissue wrap sheet, consisting of cellulose fiber kraft treated with a wet strength agent with a basis weight of 10–14 grams/meter$^2$. During testing, the tape fastening adhesive is applied to the exposed face of the polyethylene film. The film and the tissue wrap sheet may be bonded together as described in U.S. Pat. No. 5,147,347 at col. 15, lines 5 to 14, and particularly as described at col. 15, lines 14 to 60 and illustrated in the related drawing referred to in that text, and the percent coverage by the construction or laminating adhesive, is 11%, as determined by the method described in said U.S. Pat. No. 5,147,347 at col. 20, line 9 to col. 21, line 10 and illustrated in the related drawings referred to in that text, which descriptions and illustrations are incorporated by reference as if fully repeated herein. The surface roughness of the substrate is 41000±5000 Å.

Test substrate II has a peak tensile strength of about 1080 grams/inch. It is composed of a thin polyethylene film having a thickness of 1.25 mils laminated with a layer the tissue wrap sheet specified above. During testing, the tape fastening adhesive is applied to the exposed face of the polyethylene film. These layers may be bonded together in accordance with the description and illustration referred to above. The percent coverage by the construction adhesive is 49%, as determined by the method referred to above. The surface roughness of the substrate is 38000±2300 Å.

Test substrate III has a peak tensile strength of about 2550 grams/inch. It is composed of a 1.25 mil polyethylene film laminated to a 2.5 mil polypropylene film with Avery Dennison Fastape Adhesive 1112 (FT1112). The laminating adhesive covers 100% of the area of the films. During testing, the diaper tape fastening adhesive is applied to the exposed face of the polyethylene film. The surface roughness of the substrate is 41000±6000 Å. Tape backing for the tests is a 3.8 mil polypropylene film with a Young's modulus of 6.6×10$^4$ psi.

The viscoelastic properties of adhesive samples may be carried out on the Rheometrics Mechanical Spectrometer (Model RMS-800 by Rheometrics, Piscataway, N.J.) at different temperatures over a frequency range of 0.1 to 100 rad/s, using 8 mm parallel plates. The thickness of the samples is approximately 1.5 mm. The sample chamber is blanketed with nitrogen during the measurements to minimize oxidation. Master curves at two reference temperatures of 20° C. and 40° C. may be constructed from the frequency sweep date at different temperatures, using time-temperature superposition of the horizontal shift only. Good superposition of the data will be observed at the frequency range of 1 to $10^6$ rad/s.

Peak tensile strength as referred to herein may be determined by the method described in said U.S. Pat. No. 5,147,347 at col. 15, line 63 to col 16 line 14; 180° peel adhesion value may be determined by the 180° peel test method described in said patent at col. 16 line 15 to col. 17 line 10 and illustrated in the related drawings referred to in that text. These descriptions and illustrations are incorporated by reference as if fully repeated herein. It is particularly to be noted that the described measurement of 180° peel adhesion values significantly correlates to actual conditions of use, as contrasted to peel tests on a substrate adhered to a test panel at the peeling area, in that the measurement is made by peeling the tape from substrate material that is only attached to a test panel at its ends, the area of the substrate material from which the tape is peeled being unattached to the panel or any other structure.

The 180° peel test method may be performed on a MTS testing machine (Model 858 by MTS Company, Minneapolis, Minn.). The test is performed at different peel speeds to determine the transition speed for a given fastening system.

Tests 1–5 were performed on substrate I. Note that in general the higher the $(w)_{max}$, the higher the transition speed. In test 1, the $(w)_{max}$ of the adhesive is toward the lower end of the specified rheological window, and the transition speed is toward the lower end of the specified range. In test 2, only an estimated lower limit of the transition speed is noted. The transition speed could not be directly determined because the substrate was stretched before the transition speed was reached; the stretching of the substrate was due to its relatively low strength. In test 3, the $(w)_{max}$ of the adhesive is high, and so is the transition speed. In test 4, the $(w)_{max}$ of the adhesive is below the specified rheological window, and the transition speed is below the specified minimum value. In test 5, the $(w)_{max}$ of the adhesive is below the specified rheological window, and its $(\tan \delta)_{max}$ is above the window. Since higher $(\tan \delta)_{max}$ generally corresponds to higher peel adhesion, it is not surprising that the substrate tore for this adhesive.

Tests 6–15 were performed on substrate II. Again, in general, the higher the $(w)_{max}$ for the adhesives tested, the higher the transition speed. In each of tests 12 and 15, the $(w)_{max}$ of the adhesive is well below the specified rheological window, and the transition speed is also well below the specified lower limit. In test 14, the $(w)_{max}$ of the adhesive is near the lower $(w)_{max}$ limit of the specified rheological window, but the transition speed, which is correspondingly low, is somewhat below but close to the specified lower limit. Again in test 13, as in test 5 which employed the same adhesive, the high $(\tan \delta)_{max}$ was accompanied by tearing of the substrate.

Tests 16–20 were performed on substrate III. The results were consistent with the foregoing observation that, in general, the higher the $(w)_{max}$, the higher the transition speed. In all these tests, the transition speeds are somewhat higher or considerably higher than in earlier tests using the same adhesives. Compare particularly tests 18 and 19 with tests 10 and 11, respectively. This is believed to be due to the higher peel adhesions observed in the later tests, which would tend to increase transition speeds. The higher peel adhesions result from stretching of the tape backing because of the relatively high rigidity of the substrate used in the last four tests. In test 20, using the same adhesive as test 14 which has a $(w)_{max}$ near the lower $(w)_{max}$ limit of the specified rheological window, the transition speed is again correspondingly low, and in this instance, is just within the specified lower limit of transition speed.

Tests 2, 4, 7, 12 and 16 are production scale-ups, run under production conditions. The remainder of the tests are laboratory tests. Adhesive e' used in three of the production tests as indicated on the above table of test results is a scale-up whose target composition is very close to the composition of adhesive e, as may be seen from the above table of adhesives. However the rheometric data in the table of test results indicates that significant deviation from target composition caused a slight shift in $(w)_{max}$ as between adhesives e and e'. This appears to be confirmed by measurement of the glass transition temperatures ($T_g$) of the two adhesives e and e', found to be respectively −4° C. and −7.5° C.

It will be noted that the formulations of adhesives b and g are substantially identical, but test 11 shows a lower transition speed than does test 8. This is believed due to ridging or striping of the adhesive in the cross direction which occurred during the laboratory coating step in test 11.

A comparison has been made indicating that surface roughness is a factor affecting transition speed. Specifically, using the above test procedures, transition speeds were determined for current Procter & Gamble "ATTENDS" diaper tabs applied against (1) the shell of the Attends diaper as a first test substrate and (2) against substrate I as a second substrate. Surface roughnesses of these two substrates were respectively 8000±650 Å and 41000±5000 Å, and the transition speeds were found to be respectively 1700–2000 and 1000–1200, thus indicating that transition speed decreases with increasing roughness. It is believed that testing of the same tab against a substrate having a surface roughness of say 60000 Å would show an even lower transition speed.

It should be evident that this disclosure is by way of example and that various changes may be made by adding, modifying or eliminating various details without departing from the fair scope of the teaching contained in this disclosure. The invention is therefore not limited to particular details of this disclosure except to the extent that the following claims are necessarily so limited.

What is claimed is:

1. A refastenable, adhesive taping system, comprising:
   a substrate which defines a securing zone having a peak strength of less than about 2750 grams/inch, and
   an adhesive fastening tape having a flexible backing, and a layer of pressure-sensitive adhesive which is attached to said backing and is adapted to be adhered to and releasably peeled from said securing zone, said adhesive providing for a 180 degree peel adhesion of said fastening tape to said securing zone, measured at a peel speed of 2000 to 25000 mm/minute, which is less than said peak strength of said securing zone, and said adhesive having a maximum tan delta which is within the range of about 1.5 to 2.5 at 20 degrees C., reached at a frequency greater than about 500 rad/sec.

2. A taping system as recited in claim 1, wherein said substrate is provided by an outer cover of a disposable absorbent article.

3. A taping system as recited in claim 2, wherein said substrate is provided by an outer cover of a disposable diaper.

4. In a refastenable diaper, a diaper outer cover, a securing zone on the diaper outer cover of a peak strength of less than 2750 grams/inch, a refastenable adhesive taping system including an adhesive fastening tape having a factory bond section and a user bond section, said tape being fixed to said diaper at said factory bond section, said tape comprising a flexible backing and a layer of pressure-sensitive adhesive permanently combined to said flexible backing and adapted to be applied to and released from said securing zone to fasten and open the diaper at said user bond section of the tape, said adhesive exhibiting a 180° peel adhesion of the tape to the securing zone, measured at a peel speed of 2000 to 25000 mm/minute, that is less than said peak strength of the securing zone, said adhesive being selected to have a maximum tan delta of from 1.5 to 2.5 at 20° C., reached at a frequency greater than 500 rad/sec.

5. Device as in claim 4, said adhesive being selected to have a maximum tan delta of from 1.7 to 2.0 at 20° C., reached at a frequency greater than 500 rad/sec.

6. Device as in claim 5, said tape exhibiting a transition speed with respect to said securing zone of greater than 2000 mm/min.

7. Device as in claim 5, said tape exhibiting a transition speed with respect to said securing zone of greater than 3000 mm/min.

8. Device as in claim 4, said adhesive being selected to reach maximum tan delta at a frequency greater than 2000 rad/sec.

9. Device as in claim 8, said tape exhibiting a transition speed with respect to said securing zone of greater than 2000 mm/min.

10. Device as in claim 8, said tape exhibiting a transition speed with respect to said securing zone of greater than 3000 mm/min.

11. Device as in claim 4, said adhesive being selected to have a maximum tan delta of from 1.7 to 2.0 at 20° C., reached at a frequency greater than 2000 rad/sec.

12. Device as in claim 11, said tape exhibiting a transition speed with respect to said securing zone of greater than 2000 mm/min.

13. Device as in claim 11, said tape exhibiting a transition speed with respect to said securing zone of greater than 3000 mm/min.

14. Device as in claim 4, said adhesive being selected to reach maximum tan delta at a frequency greater than 3000 rad/sec.

15. Device as in claim 14, said tape exhibiting a transition speed with respect to said securing zone of greater than 2000 mm/min.

16. Device as in claim 14, said tape exhibiting a transition speed with respect to said securing zone of greater than 3000 mm/min.

17. Device as in claim 4, said adhesive being selected to have a maximum tan delta of from 1.7 to 2.0 at 20° C., reached at a frequency greater than 3000 rad/sec.

18. Device as in claim 17, said tape exhibiting a transition speed with respect to said securing zone of greater than 2000 mm/min.

19. Device as in claim 17, said tape exhibiting a transition speed with respect to said securing zone of greater than 3000 mm/min.

20. Device as in claim 4, the peak strength of said securing zone being less than 1500 grams/inch.

21. Device as in claim 20, said adhesive being selected to have a maximum tan delta of from 1.7 to 2.0 at 20° C., reached at a frequency greater than 500 rad/sec.

22. Device as in claim 21, said tape exhibiting a transition speed with respect to said securing zone of greater than 2000 mm/min.

23. Device as in claim 21, said tape exhibiting a transition speed with respect to said securing zone of greater than 3000 mm/min.

24. Device as in claim 20, said adhesive being selected to reach maximum tan delta at a frequency greater than 2000 rad/sec.

25. Device as in claim 24, said tape exhibiting a transition speed with respect to said securing zone of greater than 2000 mm/min.

26. Device as in claim 24, said tape exhibiting a transition speed with respect to said securing zone of greater than 3000 mm/min.

27. Device as in claim 20, said adhesive being selected to have a maximum tan delta of from 1.7 to 2.0 at 20° C., reached at a frequency greater than 2000 rad/sec.

28. Device as in claim 27, said tape exhibiting a transition speed with respect to said securing zone of greater than 2000 mm/min.

29. Device as in claim 27, said tape exhibiting a transition speed with respect to said securing zone of greater than 3000 mm/min.

30. Device as in claim 20, said adhesive being selected to reach maximum tan delta at a frequency greater than 3000 rad/sec.

31. Device as in claim 30, said tape exhibiting a transition speed with respect to said securing zone of greater than 2000 mm/min.

32. Device as in claim 30, said tape exhibiting a transition speed with respect to said securing zone of greater than 3000 mm/min.

33. Device as in claim 20, said adhesive being selected to have a maximum tan delta of from 1.7 to 2.0 at 20° C., reached at a frequency greater than 3000 rad/sec.

34. Device as in claim 33, said tape exhibiting a transition speed with respect to said securing zone of greater than 2000 mm/min.

35. Device as in claim 33, said tape exhibiting a transition speed with respect to said securing zone of greater than 3000 mm/min.

36. Device as in claim 20, said tape exhibiting a transition speed with respect to said securing zone of greater than 2000 mm/min.

37. Device as in claim 20, said tape exhibiting a transition speed with respect to said securing zone of greater than 3000 mm/min.

38. Device as in claim 4, said tape exhibiting a transition speed with respect to said securing zone of greater than 2000 mm/min.

39. Device as in claim 4, said tape exhibiting a transition speed with respect to said securing zone of greater than 3000 mm/min.

40. Method for manufacturing a diaper tape fastener for a diaper having a securing zone on its outer cover of a peak strength of less than 2750 grams/inch, comprising the steps of combining a tape backing and a fastening adhesive to provide an adhesive fastening tab having a 180° peel adhesion to the securing zone that is less than the peak strength of the securing zone, measured at a peel speed of 2000 to 25000 mm/minute, and joining said fastening tab to said diaper in position for deployment for adherence and release of said tab to said securing zone, including in said combining step the step of selecting said adhesive to have a maximum tan delta of from 1.5 to 2.5 at 20° C., reached at a frequency greater than 500 rad/sec.

41. Method as in claim 40, including selecting said adhesive to have a maximum tan delta of from 1.7 to 2.0 at 20° C., reached at a frequency greater than 500 rad/sec.

42. Method as in claim 40, including selecting said adhesive to reach maximum tan delta at a frequency greater than 2000 rad/sec.

43. Method as in claim 40, including selecting said adhesive to have a maximum tan delta of from 1.7 to 2.0 at 20° C., reached at a frequency greater than 2000 rad/sec.

44. Method as in claim 40, including selecting said adhesive to reach maximum tan delta at a frequency greater than 3000 rad/sec.

45. Method as in claim 40, including selecting said adhesive to have a maximum tan delta of from 1.7 to 2.0 at 20° C., reached at a frequency greater than 3000 rad/sec.

46. Method for manufacturing a diaper tape fastener for a diaper having a securing zone on its outer cover of a peak strength of less than 1500 grams/inch, comprising the steps of combining a tape backing and a fastening adhesive to provide an adhesive fastening tab having a 180° peel adhesion to the securing zone, measured at a peel speed of 2000 to 25000 mm/minute, that is less than the peak strength of the securing zone, and joining said fastening tab to said diaper in position for deployment for adherence and release of said tab to said securing zone, including in said combining step the step of selecting said adhesive to have a maximum tan delta of from 1.5 to 2.5 at 20° C., reached at a frequency greater than 500 rad/sec.

47. Method as in claim 46, including selecting said adhesive to have a maximum tan delta of from 1.7 to 2.0 at 20° C., reached at a frequency greater than 500 rad/sec.

48. Method as in claim 46, including selecting said adhesive to reach maximum tan delta at a frequency greater than 2000 rad/sec.

49. Method as in claim 46, including selecting said adhesive to have a maximum tan delta of from 1.7 to 2.0 at 20° C., reached at a frequency greater than 2000 rad/sec.

50. Method as in claim 46, including selecting said adhesive to reach maximum tan delta at a frequency greater than 3000 rad/sec.

51. Method as in claim 46, including selecting said adhesive to have a maximum tan delta of from 1.7 to 2.0 at 20° C., reached at a frequency greater than 3000 rad/sec.

\* \* \* \* \*

UNITED STATES PATENT AND TRADEMARK OFFICE
CERTIFICATE OF CORRECTION

PATENT NO. : 5,690,628
DATED : November 25, 1997
INVENTOR(S) : Richard A. Huskey et al.

It is certified that error appears in the above-identified patent and that said Letters Patent is hereby corrected as shown below:

Column 6, line 27, delete "5 . 95" and insert --5-95--.

Signed and Sealed this

Seventh Day of April, 1998

Attest:

BRUCE LEHMAN

*Attesting Officer*   *Commissioner of Patents and Trademarks*

UNITED STATES PATENT AND TRADEMARK OFFICE
CERTIFICATE OF CORRRECTION

PATENT NO. : 5,690,628
DATED : November 25. 1997
INVENTOR(S) : Richard A. Huskey, et al.

It is certified that error appears in the above-identified patent and that said Letters Patent is hereby corrected as shown below:

On the title page, item [56] insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 0 | 5 | 8 | 1 | 2 | 5 | 11/1977 | I. S. Ness | | | |

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | 0 | 4 | 4 | 0 | 1 | 6 | 3 | 8/1991 | EPO | | | | |

Signed and Sealed this

Twentieth Day of April, 1999

Attest:

Q. TODD DICKINSON

*Attesting Officer*  *Acting Commissioner of Patents and Trademarks*